US008563296B2

(12) United States Patent
Greer et al.

(10) Patent No.: US 8,563,296 B2
(45) Date of Patent: Oct. 22, 2013

(54) PROCESSES AND SYSTEMS FOR DISCHARGING AMINE BYPRODUCTS FORMED IN AN AMINE-BASED SOLVENT

(75) Inventors: David W. Greer, Cary, IL (US); Graham Ellis, Belmont, CA (US); Edward Zbacnik, Fox River Grove, IL (US); Lubo Zhou, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 309 days.

(21) Appl. No.: 12/953,865

(22) Filed: Nov. 24, 2010

(65) Prior Publication Data
US 2012/0125012 A1    May 24, 2012

(51) Int. Cl.
*C12N 1/12*    (2006.01)

(52) U.S. Cl.
USPC ........ 435/257.1; 435/183; 435/821; 435/946; 435/243

(58) Field of Classification Search
USPC .................. 435/257.1, 183, 821, 946, 243
See application file for complete search history.

(56) References Cited

U.S. PATENT DOCUMENTS

| 6,165,433 | A | 12/2000 | Chakravarti et al. |
| 2009/0028775 | A1 | 1/2009 | O—Rear |
| 2009/0049748 | A1 | 2/2009 | Day et al. |
| 2009/0162922 | A1 | 6/2009 | De Mattia et al. |
| 2010/0105126 | A1 | 4/2010 | Wright et al. |
| 2010/0170150 | A1 | 7/2010 | Walsh, Jr. |

FOREIGN PATENT DOCUMENTS

| JP | 3056121 | 3/1991 |
| WO | 2009117763 A1 | 10/2009 |

OTHER PUBLICATIONS

Shao, Renjie et al. Amines Used in CO2 Capture—Health and Environmental Impacts. The Bellona Foundation. Bellona Report. Sep. 2009. pp. 1-49. Downloaded from the Bellona organization website: <http://www.bellona.org/filearchive/fil_Bellona_report_September_2009_-_Amines_used_in_CO2_capture.pdf>.*
Department of Environmental Quality (DEQ). Aquatic Pesticides and Related Products Currently Approved for Use in Waters of the State. Downloaded from the world wide web on Jan. 11, 2013: <http://www.michigan.gov/documents/deq/wb-swas-anc-approvedherbicides_261935_7.pdf>.*
Palmer, Mervin et al. Preliminary Screening for Potential Algicides. The Ohio Journal of Science. 1955. vol. (LV)(1). pp. 1-8.*
Brown, L.M., et al., Microalgal biomass for the capture and reuse of carbon dioxide from combustion flue gases, AWMA 87th Annual Meeting (Cincinnati Jun. 19-24, 1994) Paper N.94-RA113.05 9P, Jun. 19, 1994.
Yun, Y., et al., Carbon dioxide fixation by algal cultivation using wastewater nutrients, Journal of Chemical Technology and Biotechnology, v 69, n 4, p. 451-455, Aug. 1997.
Brown, L.M., Uptake of carbon dioxide from flue gas by microalgae, Energy Conversion and Management, v 37, n 6-7, p. 1363-1367, Jun./Aug. 1996.

* cited by examiner

*Primary Examiner* — Susan Hanley
*Assistant Examiner* — Nghi Nguyen
(74) *Attorney, Agent, or Firm* — David J Piasecki

(57) ABSTRACT

Embodiments of a process for discharging amine byproducts formed in an amine-based solvent are provided. The process comprises the steps of contacting the amine-based solvent with flue gas comprising carbon dioxide, oxygen, nitrogen, $NO_x$, $SO_x$, or mixtures thereof to form a carbon dioxide-laden amine-based solvent that contains the amine byproducts. Carbon dioxide is separated from the carbon dioxide-laden amine-based solvent to form a carbon dioxide-depleted amine-based solvent. The amine byproducts from the carbon dioxide-depleted amine-based solvent are fed to an algae source.

8 Claims, 1 Drawing Sheet

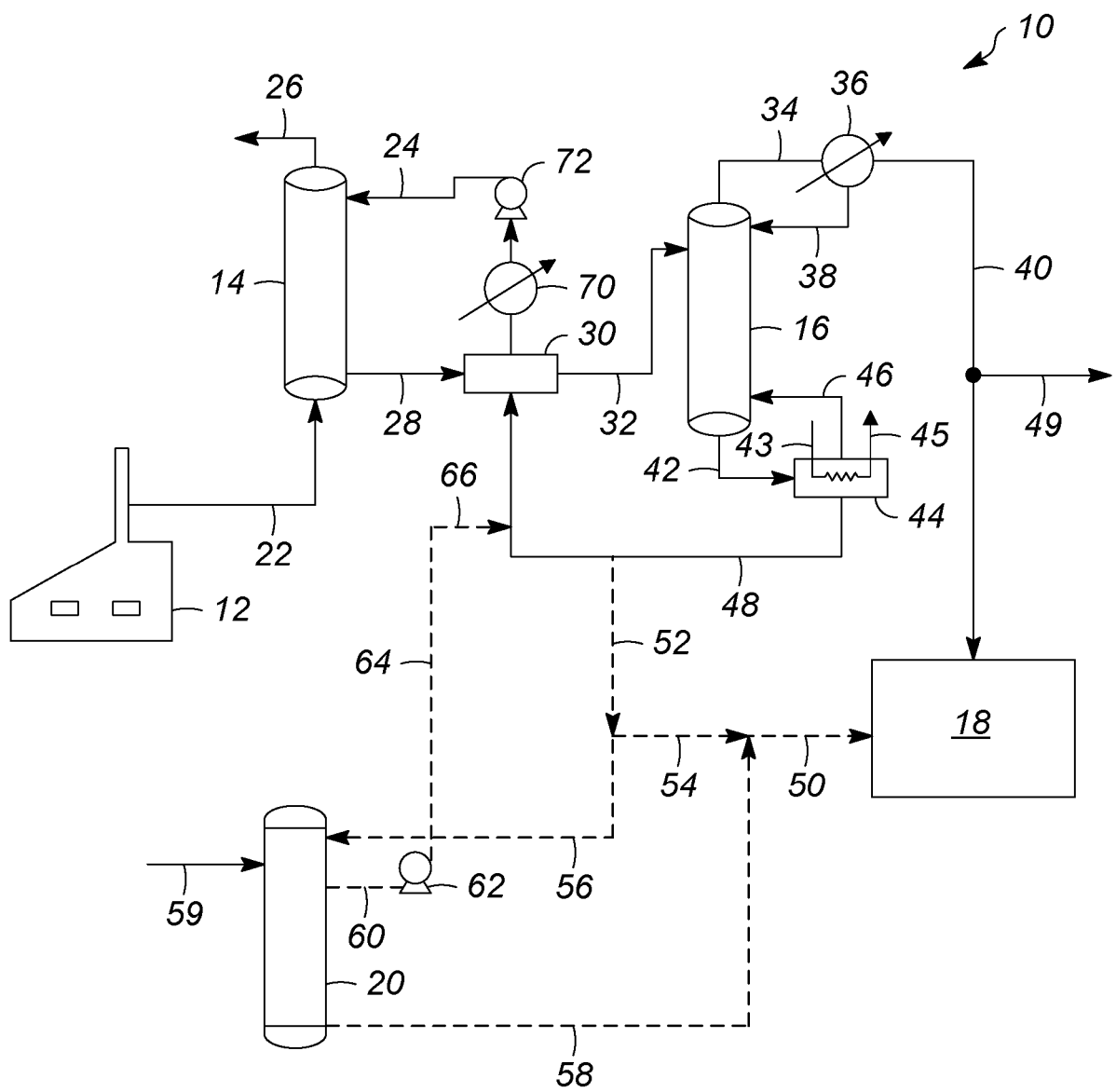

US 8,563,296 B2

PROCESSES AND SYSTEMS FOR DISCHARGING AMINE BYPRODUCTS FORMED IN AN AMINE-BASED SOLVENT

FIELD OF THE INVENTION

The present invention relates generally to processes and systems for discharging contaminants formed in a solvent, and more particularly relates to processes and systems for discharging amine byproducts formed in an amine-based solvent.

BACKGROUND OF THE INVENTION

Carbon dioxide is a well known greenhouse gas that is believed to affect global warming. Attempts to reduce emissions of carbon dioxide have focused attention on sequestering significant quantities of carbon dioxide in flue gas released from coal fired power plants, for example, as a primary means of offsetting global warming. Current methods for capturing and mitigating the entrance of carbon dioxide into the atmosphere typically use an amine-based solvent to absorb the carbon dioxide in the flue gas and then regenerate the amine-based solvent to release the carbon dioxide for sequestering and/or subsequent processing and/or conversion.

Flue gas is a mixture of various gases including for example carbon dioxide, oxygen, nitrogen, nitrous oxides ($NO_x$), sulfur oxides ($SO_x$), and water. Unfortunately, several of the gases in flue gas can react with or degrade the amine-based solvent to form contaminants, such as, for example, various amine byproducts which are problematic for many carbon dioxide absorption processes and systems. As a result, when an amine-based solvent becomes contaminated with amine byproducts, the solvent is typically purged from the system and purified for further use or treated further and disposed of as hazardous waste. Disposing the contaminated amine-based solvent as hazardous waste is both costly and environmentally objectionable. Purifying the contaminated amine-based solvent regenerates the amine-based solvent for further use. However, the contaminants removed from the solvent may need to be treated further or disposed of as hazardous waste which can be costly.

Accordingly, it is desirable to provide processes and systems for discharging the contaminants from a contaminated amine-based solvent without the high cost and environmental ramifications of current processes and systems. Furthermore, other desirable features and characteristics of the present invention will become apparent from the subsequent detailed description of the invention and the appended claims, when taken in conjunction with the accompanying drawings and this background of the invention.

SUMMARY OF THE INVENTION

Processes and systems for discharging amine byproducts formed in an amine-based solvent are provided herein. In accordance with an exemplary embodiment, a process for discharging amine byproducts formed in an amine-based solvent comprises the steps of contacting the amine-based solvent with flue gas comprising carbon dioxide, oxygen, nitrogen, $NO_x$, $SO_x$, or mixtures thereof to form a carbon dioxide-laden amine-based solvent that contains the amine byproducts. Carbon dioxide is separated from the carbon dioxide-laden amine-based solvent to form a carbon dioxide-depleted amine-based solvent. The amine byproducts from the carbon dioxide-depleted amine-based solvent are fed to an algae source.

In accordance with another exemplary embodiment, a system for discharging amine byproducts formed in an amine-based solvent is provided. The system comprises a carbon dioxide absorber unit configured to contact the amine-based solvent with flue gas comprising carbon dioxide, oxygen, nitrogen, $NO_x$, $SO_x$, or mixtures thereof to form a carbon dioxide-laden amine-based solvent that contains the amine byproducts. A stripper unit is in fluid communication with the carbon dioxide absorber unit and is configured to separate the carbon dioxide from the carbon dioxide-laden amine-based solvent to form a carbon dioxide-depleted amine-based solvent. An algae source is for receiving the amine byproducts from the carbon dioxide-depleted amine-based solvent.

BRIEF DESCRIPTION OF THE DRAWINGS

Embodiments of the present invention will hereinafter be described in conjunction with the following drawing figures, wherein like numerals denote like elements, and wherein:

FIG. 1 schematically illustrates a system for discharging amine byproducts formed in an amine-based solvent in accordance with an exemplary embodiment.

DETAILED DESCRIPTION

The following Detailed Description is merely exemplary in nature and is not intended to limit the invention or the application and uses of the invention. Furthermore, there is no intention to be bound by any theory presented in the preceding Description of Related Art or the following Detailed Description.

Various embodiments contemplated herein relate to processes and systems for discharging amine byproducts formed in an amine-based solvent that is used for absorbing carbon dioxide from flue gas. In a carbon dioxide absorber unit, the amine-based solvent is contacted with flue gas that typically comprises carbon dioxide, oxygen, nitrogen, nitrous oxides ($NO_x$), sulfur oxides ($SO_x$), and other gaseous components and particulates. The amine-based solvent readily absorbs the carbon dioxide as well as some of the other gaseous components of the flue gas. However, over time and continuous recycling through the carbon dioxide absorber unit and a carbon dioxide stripper unit that separates the carbon dioxide from the solvent, some of the other gaseous components absorbed from the flue gas will tend to break down or degrade the amine-based solvent forming various amine byproducts, such as, for example, nitrogen-based compounds, amine salts including heat stable amine salts (HSAS), and sulfur-based compounds. When this occurs, the amine-based solvent from the absorber unit will be laden not only with carbon dioxide but also with the amine byproducts. As such, when carbon dioxide is subsequently separated from the carbon dioxide-laden amine-based solvent in the carbon dioxide stripper unit, the carbon dioxide-depleted amine-based solvent will contain the amine byproducts.

The inventors have discovered that many of these amine byproducts as well as the amine-based solvent are readily consumable nutrients for algae. In an exemplary embodiment, the amine byproducts from the carbon dioxide-depleted amine-based solvent are fed to an algae source for digestion by the algae. Thus, the amine byproducts are discharged without being disposed of as hazardous waste. Furthermore, the cost of maintaining an algae source is nominal especially if the algae source is already on site and being used to consume carbon dioxide from the flue gas for photosynthesis.

In another exemplary embodiment, the amine byproducts are introduced to a reclaimer unit prior to being fed to the algae source. The reclaimer unit separates the amine byproducts from the carbon dioxide-depleted amine-based solvent to form a regenerated amine-based solvent and an amine byproducts effluent. In this embodiment, the amine byproducts effluent is fed to the algae source and the regenerated amine-based solvent is preferably introduced back to the carbon dioxide absorber unit, and thus, disposal of the amine-based solvent as hazardous waste is avoided.

Referring to FIG. 1, a schematic depiction of an exemplary system for discharging amine byproducts formed in an amine-based solvent is provided. The system 10 comprises a flue gas source 12, such as, for example, a carbonaceous burning power plant, a carbon dioxide absorber unit 14, a stripper unit 16 and an algae source 18. Preferably, the system 10 also comprises a reclaimer unit 20. Flue gas from the flue gas source 12 is introduced to the carbon dioxide absorption unit 14 preferably near a bottom via line 22. The flue gas typically comprises a mixture of gases including carbon dioxide, oxygen, nitrogen, $NO_x$, $SO_x$, water vapor, trace amounts of hydrocarbons, hydrogen and carbon monoxide, and particulates.

The carbon dioxide absorber unit 14 is operating preferably at a temperature of from about 40 to 50° C. at the top and at a temperature of from about 50 to about 60° C. at the bottom. An amine-based solvent is introduced to the carbon dioxide absorption unit 14, for example, near a top via line 24. In an exemplary embodiment, the amine-based solvent comprises an amine selected from the group consisting of monoethanolamine, diethanolamine, piperazine, diisopropanolamine, triethanolamine, 2-amino,2-methyl,1-propanol, diamines, methyldiethanolamine, tertiary amines, and mixtures thereof. In one example, the amine-based solvent comprises from about 5 to about 30 weight percent of one or more faster reaction rate amines, which require relatively less contact time with the flue gas to absorb carbon dioxide, and from about 5 to about 50 weight percent of one or more slower reaction rate amines, which require relatively more contact time with the flue gas to absorb carbon dioxide. Examples of faster reaction rate amines include monoethanolamine, diethanolamine, piperazine, and diisopropanolamine. Examples of slower reaction rate amines include methyldiethanolamine, triethanolamine, and sterically hindered amines such as 2-amino,2-methyl,1-propanol. In another example, the total amine concentration in the amine-based solvent, whether or not a slower or faster reaction rate amine is present, is of from about 20 to about 80 weight percent, preferably of from about 30 to about 50 weight percent. In addition to water, the amine-based solvent may also contain others species such as diamines and tertiary amines.

Contacting of the amine-based solvent with flue gas occurs within the carbon dioxide absorption unit 14 as the flue gas rises in countercurrent flow against the downward flowing amine-based solvent. The carbon dioxide absorption unit 14 may contain column internals or mass transfer elements such as trays or random or structured packing. As the flue gas rises, carbon dioxide within the flue gas is absorbed into the downward flowing amine-based solvent resulting in a carbon dioxide depleted top vapor at the top of the carbon dioxide absorption unit 14, and a carbon dioxide-laden amine-based solvent at the bottom of the carbon dioxide absorption unit 14.

As discussed previously, over time, continuous use and/or recycling, some of the gaseous components in the flue gas will tend to break down the amine-based solvent into various amine byproducts. In particular, oxygen, $NO_x$, and $SO_x$ from the flue gas substantially contribute to the degradation of the amine-based solvent. Accordingly, a "well used" or "worn-out" amine-based solvent will contain the amine byproducts when it absorbs the carbon dioxide from the flue gas in the carbon dioxide absorption unit 14 and forms a carbon dioxide-laden amine-based solvent. In an exemplary embodiment, the amine byproducts comprise compounds selected from the group consisting of nitrogen-based compounds, bicine, amino acids, amine salts, sulfur-based compounds, thiosulfates, dithiocarbanates, thioureas, polysulfides, and mixtures thereof.

The top vapor is withdrawn from the upper portion of the carbon dioxide absorption unit 14 in a gas stream through line 26. The carbon dioxide-laden amine-based solvent is withdrawn from the lower portion of the carbon dioxide absorption unit 14 in a stream through line 28, and is passed through a heat exchanger 30 where it is heated to a temperature preferably of from about 90 to about 120° C., and more preferably of from about 100 to 110° C.

The heated carbon dioxide-laden amine-based solvent is passed from the heat exchanger 30 through line 32 into the upper portion of a stripping unit 16 which is operating preferably at a temperature of from about 100 to about 110° C. at the top and at a temperature of from about 115 to about 125° C. at the bottom. In an exemplary embodiment, as the carbon dioxide-laden amine-based solvent flows down through the stripping unit 16 over mass transfer elements, which can be trays or random structured packing, carbon dioxide is stripped from the amine solvent by an upward flowing vapor, which is generally steam, to produce a carbon dioxide rich top vapor and an amine recovery solvent containing a carbon dioxide-depleted amine-based solvent including the amine byproducts, and water. The carbon dioxide rich top vapor is withdrawn from the upper portion of the stripping unit 16 through line 34 and passed to a reflux condenser 36 where it is separated into carbon dioxide gas and condensates. The condensates, which comprise primarily water and amines, may be returned to the upper portion of the stripping unit 16 via line 38. In an exemplary embodiment, the carbon dioxide gas is introduced to the algae source 18 via line 40 for consumption by the algae for photosynthesis. A portion of the carbon dioxide gas may also be passed along line 49 for other uses.

The amine recovery solvent is withdrawn from the lower portion of the stripping unit 16 through line 42 and passed to a reboiler 44 where it is heated to a temperature preferably of from about 115 to about 125° C. In one example, the reboiler 44 is driven by saturated steam 43 at a pressure of about 1.9 bar (about 28 psig) or higher, which is withdrawn from the reboiler 44 in stream 45. The heating of the amine recovery solvent in the reboiler 44 drives off the water which is passed as steam in line 46 into the lower portion of the stripping unit 16 where it serves as the aforementioned upward flowing vapor. The resulting amine recovery solvent is the carbon dioxide-depleted amine-based solvent containing the amine byproducts and is withdrawn from the reboiler 44 through line 48.

In one exemplary embodiment, the carbon dioxide-depleted amine-based solvent is purged from line 48 at a suitable outlet point and is collected as a batch where the batch is fed to the algae source 18 through line 50. The algae source 18 may be a suitably sized body of water containing algae, such as a pond, or other suitable environment for supporting algae known to those skilled in the art. In another exemplary embodiment, the carbon dioxide-depleted amine-based solvent is fluidly communicated from line 48 to the algae source 18 via lines 52, 54 and 50. In either of these exemplary embodiments, the amine byproducts are fed to the algae source together with the remaining portion of the carbon dioxide-depleted amine-based solvent but separately from the carbon dioxide gas, which is fed to the algae source via line 40. Since the amine-based solvent is typically basic and the algae in the algae source 18 prefers neutral to moderate basic conditions, preferably the carbon dioxide-depleted amine-based solvent is introduced to the algae source 18 at a suitable mass rate so as to not cause the algae source 18 to have a pH exceeding about 11.

In an exemplary embodiment, the amine byproducts or at least a portion of the amine byproducts are nutrients for the algae and are readily digested by the algae source 18. Moreover, the carbon dioxide-depleted amine-based solvent may also be nutrients for the algae, and accordingly, may be readily digested by the algae source 18. In another exemplary embodiment, the algae source 18 contains bacteria that are effective to convert at least portions of amine byproducts and/or the carbon dioxide-depleted amine-based solvent into nutrients for consumption by the algae source 18.

In another exemplary embodiment, the carbon dioxide-depleted amine-based solvent is introduced to the reclaimer unit 20 for separation of the amine byproducts from the solvent prior to introduction to the algae source 18. In one example, the carbon dioxide-depleted amine-based solvent is purged from line 48 and collected as a batch which is introduced to the reclaimer unit 20. In another example, the carbon dioxide-depleted amine-based solvent is fluidly communicated from line 48 to the reclaimer unit 20 through lines 52 and 56.

In an exemplary embodiment, the reclaimer 20 operates in a semi-continuous batch mode. At the start of a reclaiming cycle, the carbon dioxide-depleted amine-based solvent is charged to the reclaimer 20, preferably diluted with water from line 59, to establish a liquid level. As the solvent is distilled, additional carbon dioxide-depleted amine-based solvent is fed to the reclaimer 20 to maintain the liquid level. Initially, the overhead vapor in the reclaimer 20 is mostly water. As the distillation continues, the liquid and vapor phases become more and more concentrated with the amine-based solvent. The amine byproducts accumulate as an effluent in the bottom of the reclaimer 20 and the boiling temperature of the liquid phase continues to rise until the condensing temperature remains that of the pure amine-based solvent and water. In one example, to ensure effective reclaimer operation, a temperature is specified as the cut off temperature for the reclaimer 20 defining the endpoint for distillation. To recover more amine-based solvent, the solution may then be diluted again with water to lower the boiling point temperature and the batch distillation is continued until the end point temperature is again achieved. Multiple reclaiming cycles may be used to achieve the desired level of purity, thereby producing a regenerated amine-based solvent.

In an exemplary embodiment, the amine byproducts effluent, which contains the amine byproducts, is fed to the algae source 18 for digestion by the algae. In one example, the amine byproducts effluent is purged from the reclaimer unit 20 as a batch which is fed to the algae source 18 via line 50. In another example, the amine byproducts effluent is fluidly communicated from the reclaimer unit 20 to the algae source 18 via lines 58 and 50.

In an exemplary embodiment, the regenerated amine-based solvent is introduced back to the absorber unit 14 by any number of suitable pathways in the system 10. In one example, the regenerated amine-based solvent is withdrawn from the reclaimer unit 20 and passed to pump 62 via line 60. The pump 62 advances the regenerated amine-based solvent through lines 64, 66 and 48 to the heat exchanger 30, where it provides at least a portion of heat for heating the aforementioned carbon dioxide-laden amine-based solvent stream, and from it emerges partially cooled. The partially cooled regenerated amine-based solvent is then passed through the cooler 70, which cools the solvent, forming a cooled regenerated amine-based solvent. As illustrated, a pumped 72 advances the cooled regenerated amine-based solvent to the absorber unit 14.

Accordingly, processes and systems for discharging amine byproducts formed in an amine-based solvent have been described. The various embodiments comprise contacting the amine-based solvent with flue gas in a carbon dioxide absorber unit to form a carbon dioxide-laden amine-based solvent that contains the amine byproducts. The carbon dioxide is separated from the carbon dioxide-laden amine-based solvent to form a carbon dioxide-depleted amine-based solvent. The amine byproducts from a carbon dioxide depleted amine-based solvent are fed to an algae source for digestion by the algae. Accordingly, the amine byproducts do not need to be disposed of as hazardous waste, which would otherwise be environmentally objectionable. Furthermore, the cost of maintaining an algae source is nominal especially if the algae source is already on site and being used to consume carbon dioxide for photosynthesis. Moreover, a reclaimer unit may be used to separate the amine byproducts from the carbon dioxide-depleted amine-based solvent prior to being fed to the algae source to form a regenerated amine-based solvent and an amine byproducts effluent. In this embodiment, the amine byproducts effluent is fed to the algae source and the regenerated amine-based solvent is preferably introduced back to the carbon dioxide absorber unit, and thus, the amine-based solvent does not need to be disposed of as hazardous waste.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

What is claimed is:

1. A process for discharging amine byproducts formed in an amine-based solvent, the process comprising the steps of:
 a) contacting the amine-based solvent with flue gas comprising carbon dioxide, oxygen, nitrogen, $NO_x$, $SO_x$, or mixtures thereof to form a carbon dioxide-laden amine-based solvent that contains at least one amine byproduct selected from the group consisting of bicine, thiosulfates, thioureas, polysulfides, and mixtures thereof;
 b) separating carbon dioxide from the carbon dioxide-laden amine-based solvent to form a carbon dioxide-depleted amine-based solvent; and
 c) feeding at least one of the amine byproducts from the carbon dioxide-depleted amine-based solvent to an algae source.

2. The process according to claim 1, wherein the amine-based solvent comprises an amine selected from the group consisting of monoethanolamine, diethanolamine, piperazine, diisopropanolamine, triethanolamine, 2-amino,2-methyl,1-propanol, diamines, methyldiethanolamine, tertiary amines, and mixtures thereof.

3. The process according to claim 1, further comprising the step of separating the amine byproducts from the carbon dioxide-depleted amine-based solvent to form a regenerated amine-based solvent and an amine byproducts effluent, and wherein the step of feeding includes introducing the amine byproducts effluent to the algae source.

4. The process according to claim 3, wherein the step of separating carbon dioxide includes forming a carbon dioxide rich stream from the carbon dioxide separated from the carbon dioxide-laden amine-based solvent, and the process further comprising the step of introducing the carbon dioxide rich stream to the algae source.

5. The process according to claim 3, wherein the step of contacting the amine-based solvent with the flue gas occurs in a carbon dioxide absorber unit, and the process further comprising the step of introducing the regenerated amine-based solvent to the carbon dioxide absorber unit.

6. The process according to claim 1, wherein the step of feeding includes introducing the carbon dioxide-depleted amine-based solvent to the algae source, the carbon dioxide-depleted amine-based solvent containing the amine byproducts.

7. The process according to claim 6, wherein the step of feeding includes introducing a quantity of the carbon dioxide-depleted amine-based solvent to the algae source, the quantity sufficiently limited so as to not cause the algae source to have a pH exceeding about 11.

8. The process according to claim 1, wherein at least a portion of the amine byproducts are nutrients for algae in the algae source, and the process further comprising the step of digesting the nutrients with the algae.

* * * * *